United States Patent
Breen et al.

(10) Patent No.: US 6,677,765 B2
(45) Date of Patent: Jan. 13, 2004

(54) DETECTION, MEASUREMENT AND CONTROL OF AMMONIA IN FLUE GAS

(75) Inventors: Bernard P. Breen, Pittsburgh, PA (US); James E. Gabrielson, Hanover, MN (US); David Eden, Aberdeenshire (GB)

(73) Assignee: ESA Corrosion Solutions, LLC, Lawrence, PA (US)

( * ) Notice: Subject to any disclaimer, the term of this patent is extended or adjusted under 35 U.S.C. 154(b) by 65 days.

(21) Appl. No.: 10/114,362

(22) Filed: Apr. 2, 2002

(65) Prior Publication Data

US 2003/0184320 A1 Oct. 2, 2003

(51) Int. Cl.[7] .............................................. G01R 27/08
(52) U.S. Cl. ..................................... 324/691; 324/700
(58) Field of Search ........................ 110/345; 324/691, 324/700; 423/235, 239.1

(56) References Cited

U.S. PATENT DOCUMENTS

| | | | |
|---|---|---|---|
| 4,575,678 A | | 3/1986 | Hladky |
| 5,078,064 A | | 1/1992 | Breen et al. |
| 5,139,627 A | * | 8/1992 | Eden et al. ............... 205/775.5 |
| 5,181,475 A | | 1/1993 | Breen et al. |
| 5,746,144 A | | 5/1998 | Breen et al. |
| 5,854,557 A | * | 12/1998 | Tiefnig ........................ 324/700 |
| 5,915,310 A | | 6/1999 | Hura et al. |
| 6,030,204 A | | 2/2000 | Breen et al. |
| 6,048,510 A | * | 4/2000 | Zauderer ..................... 423/235 |
| 6,117,403 A | * | 9/2000 | Alix et al. ................... 423/210 |
| 6,132,593 A | * | 10/2000 | Tan ........................... 205/776.5 |
| 6,203,598 B1 | * | 3/2001 | Hasegawa et al. ............. 95/92 |
| 6,475,350 B2 | * | 11/2002 | Palekar et al. .............. 204/164 |
| 6,478,948 B2 | * | 11/2002 | Breen et al. ................ 205/740 |

* cited by examiner

*Primary Examiner*—N. Le
*Assistant Examiner*—Walter Benson
(74) *Attorney, Agent, or Firm*—Buchanan Ingersoll, P.C.

(57) ABSTRACT

A tubular probe has spaced apart bands or patches of the same material as the probe body attached to the probe body by an electrically insulating, high temperature material. A series of cooling tubes are provided within the probe body to direct cold air to the regions near each band. One or more probes is placed in a furnace or boiler above the ammonia injection zone. When ammonium bisulfate forms on the probe it completes an electrical circuit between the probe body and the bands and will also cause corrosion of the probe. The presence of ammonium bisulfate is detected by a change in resistance between the bands and the probe body. Electrochemical noise is generated during the corrosion process. A corrosion rate can be determined from the level or amount of electrochemical noise that is detected.

22 Claims, 2 Drawing Sheets

DETECTION, MEASUREMENT AND CONTROL OF AMMONIA IN FLUE GAS

FIELD OF THE INVENTION

This invention relates to the detection of ammonia or to the detection of the ill effects of ammonia in flue gas.

BACKGROUND

Ammonia is in common use today as a reactant for the removal of nitrogen oxides from gas streams. When it is injected it reacts with nitric oxide (NO) to form $N_2$ and $H_2O$ and thereby reduces the emissions of the undesirable nitrogen oxides. It is usually used in concentrations about as large as the NO concentration.

Two common methods are used to speed the reactions between ammonia $NH_3$ and NO. In one case a high temperature is used. Temperatures of about 1600° F. to 1900° F. are used to speed the reaction. After this reaction the gases, if they are from combustion in a boiler, pass through several heat exchange devices and they eventually exit the stack at about 270° F. to 370° F. The gases from some older boilers may exit the stack at higher temperatures, but for efficiency it is necessary to have low stack temperatures. This type of process is known as Thermal deNOx or Selective Non-Catalytic Reduction (SNCR). In another case a catalyst is used to speed the reaction. Even so the catalyst bed may be at around 700° F. This process is known as Selective Catalytic Reduction (SCR). Subsequent to the reduction, the gas is cooled to the same temperatures as in the Thermal deNOx systems.

In either of these processes some of the $NH_3$ passes through the reaction zone and out of the stack along with the flue gas. It is undesirable to have $NH_3$ in the flue gas as it is seen as an undesirable emission and in many places there are regulations limiting the $NH_3$ emissions. The odor of ammonia is objectionable. When the ammonia is too high some will be absorbed by the fly ash. The ash then has the odor of ammonia and must be disposed of rather than used in concrete. This adds an expense to the operation of the boiler.

$NH_3$ also reacts with chlorine or hydrochloric acid, either of which may be in flue gas from the combustion of coal and are usually in the combustion of refuse and some wood waste. The reaction forms ammonium chloride ($NH_4Cl$). $NH_4Cl$ forms as a very fine particle or fume, which makes an objectionable visible emission. Also, the $NH_4Cl$ can plug various heat exchange devices and stop the flow of the flue gas.

Most importantly the $NH_3$ reacts with sulfur trioxide ($SO_3$) to form ammonium sulfate (($NH_4)_2SO_4$) or ammonium bisulfate ($NH_4)HSO_4$. They both can plug heat transfer devices especially the regenerative air heater, which has many small passages. This plugging can restrict the flow of the air and the flue gas so severely that the boiler must be taken off-line and the air heater cleaned. The ammonium bisulfate is much the worst offender of the two as it is very sticky through much of the exhaust gas temperature range. The problem may be exacerbated by the SCR process that converts some of the $SO_2$ to $SO_3$. Also, the ammonia may react with $SO_2$ and oxygen to form these ammonium sulfates. Since the $SO_2$ is much more abundant (about 50 to 1) than the $SO_3$ all of the ammonia present in flue gas is likely to react and form an ammonium sulfate.

By whatever process the ammonia reacts or how ammonium sulfates are formed, all of the ammonium salts that are present in the flue gas can cause fouling of heat exchanger surfaces and plugging of the heat exchangers. This shuts down the operation. Ammonium bisulfate is the worst offender since it melts at 296° F. Ammonium sulfate is solid to 955° F. where it decomposes and ammonium chloride is solid to 662° F. where it decomposes. Thus, while any of these salts can cause fouling, only the ammonium bisulfate will exist in the liquid state in the boiler and the liquid is the source of the greatest fouling problem.

The fouling of heat transfer surfaces by liquid ammonium bisulfate and the solid particles that are imbedded in the liquid can become very severe at temperatures above 296° F. The ammonium bisulfate decomposes at high temperatures, maybe as high as 914° F. and the fouling problem could extend to temperatures this high.

Ammonium bisulfate, which is often called ammonium acid sulfate is acidic and can cause corrosion especially in the presence of water. Thus, the molten ammonium bisulfate may cause a water dew-point at temperatures significantly above its melting point of 296° F. In that case, the water present in the flue gas is induced, by the ammonium bisulfate, to condense at higher and higher temperatures where it should not normally condense. This water dew point further aggravates the fouling tendencies of the ammonium bisulfate in that it allows for the condensation of a sticky water-soluble material which in turn causes fly ash to also accumulate (or foul) at temperatures above 296° F. How far above this temperature that fouling occurs is a measure of the fouling tendency caused by an excess of ammonia.

To eliminate the plugging it is necessary to eliminate the formation of ammonium sulfates in the flue gas. The sulfur as well as chlorine are in the fuel whether it is coal, oil, waste or other combustible material. Consequently, to prevent heat exchanger plugging as well as to reduce emissions of ammonia and prevent this source of corrosion it is necessary to reduce the amount of ammonia (i.e., ammonia slip) that passes through the SNCR or SCR process. To do this, it is very important to be able to measure either the ammonia slip or the resulting fouling tendency. Typically, ammonia is introduced into flue gas at multiple locations around the circumference of the stack to reduce $NO_x$. The problem with reducing the ammonia is that it is essential for the $NO_x$ reduction processes. Because ammonia is introduced at multiple locations and because of turbulence and cross currents in the flue gas, the concentration of ammonia may be too high in one location and not high enough in another part of the process. A measurement device is needed to find the ammonia concentrations on a spatial basis and in real time. Instruments that are available for the measurement of ammonia have not been reliable and wet chemical analysis of the gas for ammonia is too slow for control purposes. If there were a reliable instrument and method for measuring ammonia slip on a spatial basis in real time, the ammonia slip measurement could then be used to optimize the spatial injection of ammonia into any combination of SNCR and SCR processes.

SUMMARY OF THE INVENTION

We provide a method of measuring ammonia in flue gas by using a cooled probe to measure conductivity (and corrosion) caused by condensed ammonium bisulfate. The process will work for any fuel with a significant concentration of sulfur, i.e., where there is potential for the fouling and corrosion problem to occur. The method and probe may also reveal those circumstances where there is no problem in fouling or corrosion occurring. It will be most useful in furnaces or boilers where the operator is injecting ammonia to reduce $NO_x$ emissions. The use of this method and device will allow the boiler operator to use as much ammonia as is required to substantially eliminate NO emissions without fear of fouling the boiler back passes and without excessive ammonia emissions.

We prefer to provide a tubular probe having spaced apart bands or patches of the same material as the probe body. The bands or patches are attached to the probe body by an electrically insulating, high temperature material. At least one thermocouple is attached to the probe. A series of cooling tubes are provided within the probe body to direct cold air to the regions near each band. One or more probes is placed in the furnace or boiler above the ammonia injection zone. When ammonium bisulfate forms on the probe it completes an electrical circuit between the probe body and the bands. Hence, the presence of ammonium bisulfate can be detected by a change in resistance between the bands and the probe body. The ammonium bisulfate will also cause corrosion of the probe. Electrochemical noise is generated during the corrosion process. A monitor connected to the probe body can detect any change in resistance as well as electrochemical noise. Furthermore, a corrosion rate can be determined from the level or amount of electrochemical noise that is detected.

Information obtained from the probe can be correlated with the position of the probe to identify those injectors that may be the source of the detected excess ammonia. Then the injectors can be adjusted to reduce or eliminate excess ammonia injection.

Other objects and advantages of the present invention will become apparent from the description of certain present preferred embodiments thereof that are shown in the drawings.

DESCRIPTION OF THE PREFERRED EMBODIMENTS

Figure 1:
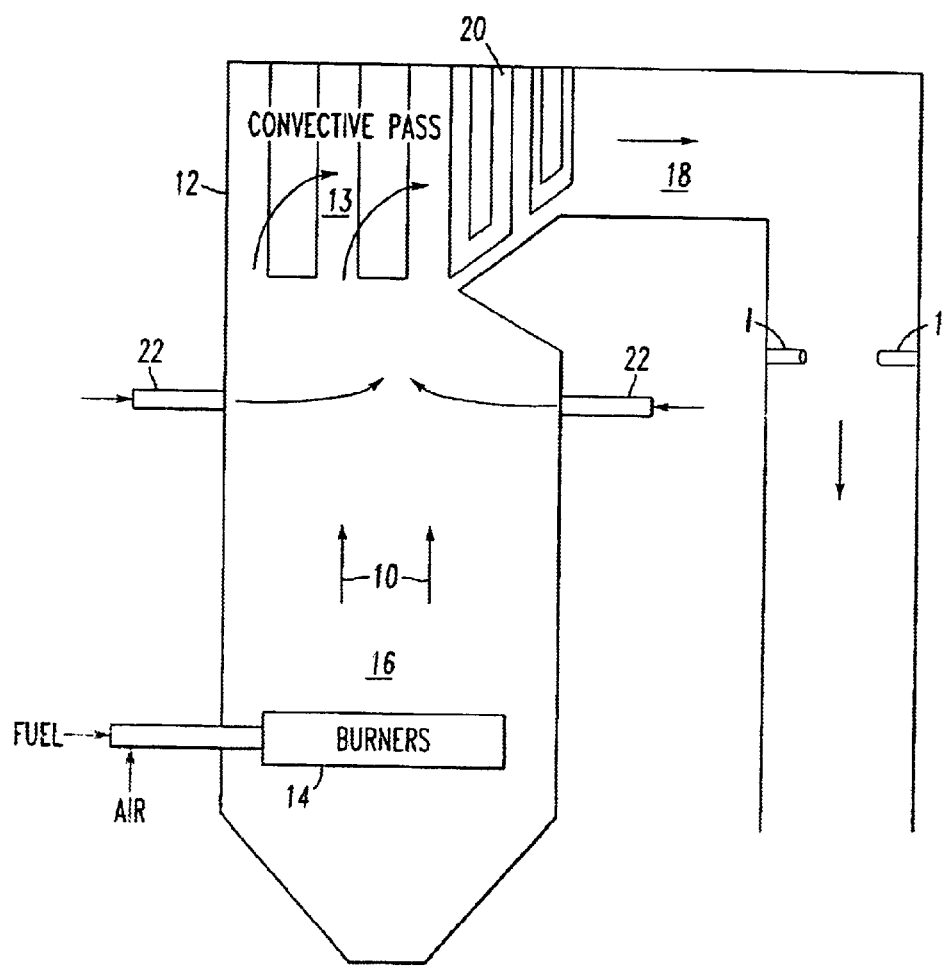
FIG. 1 is a schematic of a typical furnace or bottom fired boiler in which the probes of the present invention are positioned to detect ammonia concentration and fouling of heat exchangers.

Referring to FIG. 1, a typical furnace or boiler 12 is designed to utilize coal or any other fuels such as oil or gas. The fuel and combustion air enter the combustion device through burners 14 which are shown here in the lower portion of the combustion device 12. The fuel burns in the primary combustion zone 16 of the device within which temperatures are typically in excess of 3000° F. Combustion products 10 flow upward from the combustion zone 16, through convective pass 13, past convective heat exchangers 20, through duct work 18 and out of the furnace. Because of heat loss to furnace walls, the flue gas has a temperature of only 1800° F. to 2500° F. when it exits the furnace near the heat exchanger 20. Heat exchangers 20 in the upper portion of the furnace cause the temperature to drop very rapidly and any unburned fuel which enters these heat exchangers usually will be wasted and will exit the furnace as hydrocarbon emissions. One method of reducing hydrocarbon emissions is to introduce ammonia into the upper furnace through injectors 22 that are located around the walls of the furnace. If too much ammonia is injected the excess ammonia will react with sulfur compounds and chlorine in the flue gas to form corrosive compounds that are deposited on the heat exchangers causing fouling. We therefore provide a set of probes 1 that are placed in the furnace or boiler above the region in which the ammonia is injected. We prefer to place several probes in the flue gas stream. By using multiple probes in the boiler it will be possible to determine if there are specific locations where the ammonia flow is excessive. In those cases it will often be possible to reduce the ammonia flow in specific zones and eliminate fouling without increasing NO emissions. Although we prefer to use the probe in the boiler or furnace as shown in FIG. 1, it is also possible to place the probe in a slip stream drawn from the furnace. The probe could also be used with flue gas generated in a test apparatus or other laboratory setting.

The probes will be in the hot gas stream but they will be cooled to the condensation point of the ammonium bisulfate water dew point. We prefer to cool the probes by blowing air through them. A thermocouple or other temperature-sensing device will be used to detect the temperature. The airflow will be automatically modulated to adjust the temperature within the desired range.

Figure 2:
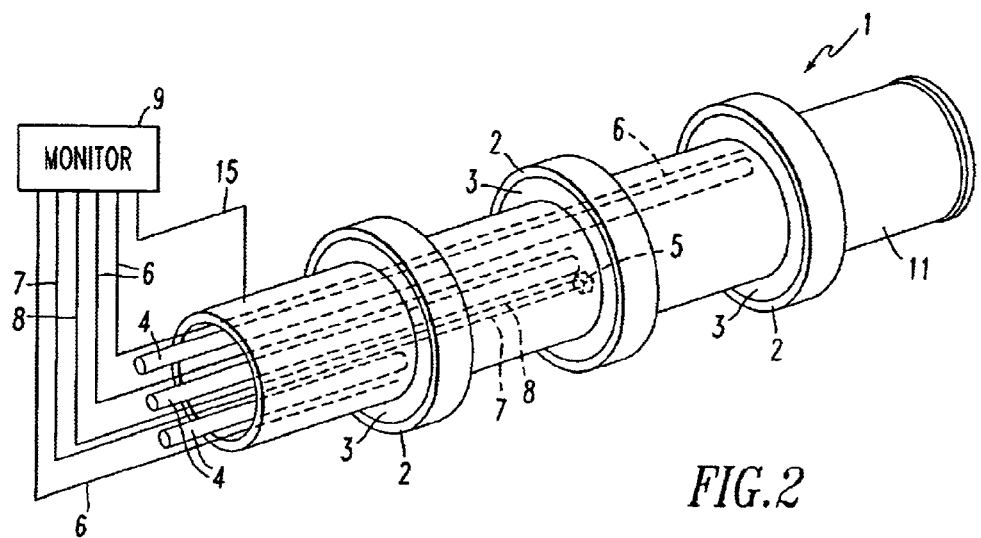
FIG. 2 is a perspective view of a present preferred embodiment of a probe in accordance with the present invention.

A present preferred embodiment of the probe with air-cooling and temperature measurement and airflow feedback is shown in FIG. 2. The air-cooled probe 1 consists of a tubular body 11 made of an electrically conductive metal, typically steel. A nickel-chromium steel alloy could be used. Indeed, the probe could be made of the same metal as is used for the heat exchangers in the boiler. There is at least one and preferably multiple insulated bands 2 of the same material as the hollow tube probe body 11 positioned at spaced apart locations and encircling the probe body. The bands are electrically insulated from the body by high temperature insulating material 3. Air-cooling tubes 4 extend internal to the hollow tube probe 1 to the exact region of each band 2. A thermocouple 5 is provided near one band 2 to measure the band temperature in this region. Electrical connecting wires 6 from each band and thermocouple wires 7 and 8 from the thermocouple 5 extend back to the hollow tube probe exit. Although only one thermocouple is provided in the embodiment of FIG. 1. it should be understood that more than one thermocouple could be used. Air-cooling tubes and the airflow from the band region also exit the probe here.

One or more probes 1 are positioned in the furnace above the ammonia injection region. The probes are cooled to a temperature below 914° F. and above 296° F. Any excess ammonium in the flue gas can react with sulfur trioxide in the flue gas to form ammonium sulfate and ammonium bisulfate. Since ammonium sulfate is liquid between 296° F. and 914° F., any excess ammonia in the flue gas will react with sulfur trioxide in the region of the probe forming a liquid deposit on the probe. The presence of that liquid between the probe body 11 and an electrical band 2 completes an electrical circuit. In this way the bands 2 and probe body 11 function as pairs of spaced apart electrodes. A monitor 9 is connected to the bands by wires 6 and is also connected to the probe body 11 by wire 15. The monitor detects changes in resistance between the spaced apart electrodes. The presence of ammonium bisulfate on the probe will cause corrosion of the probe metal. That corrosion produces electrochemical activity that is detected by the monitor. The monitor 9 converts electrochemical activity detected by the electrodes 1, 2 into a relative conductivity or corrosion rate. The technique is described in U.S. Pat. No. 4,575,678 to Hladkey and U.S. Pat. No. 5,139,627 to Eden et al. A corrosion monitor available from InterCorr International and under the name SmartCET could be used.

The presence of a condensed liquid phase will be determined by the resistance between two electrodes. Without a condensed phase the resistance will be very high and with a liquid phase the resistance will be very low. With ammonium bisulfate in the gas the resistance should decrease slightly as the temperature is decreased below 914° F. but decrease suddenly when water begins to condense (at its ammonium bisulfate dew-point) as the temperature decreases to 296° F., below which point the ammonium bisulfate will become solid. The solid will have a higher resistivity than the liquid, but it will not be anywhere nearly as high as the resistivity of the gas. Lower melting points, below 296° F., will occur with impurities such as ammonium chloride but these are also a measure of ammonia slip and detrimental fouling, which are to be avoided by the adjustment of ammonia injection. Even at the higher temperatures above 296° F. liquid ammonium compound condensate will be detected from impurities, which will cause aqueous dew-points. It is the purpose of this probe to detect such fouling condensate so that the relative volume of ammonia which causes fouling has been detected and can be adjusted, in order to alleviate the exact amount of ammonia slip which causes the back-end fouling problem in that region of the spatially non-uniform flow.

Air-cooling is applied until low resistivity is detected at the insulated band 2. At this point, the fouling temperature and the relative ammonia slip concentration have been measured. The probe will be allowed to heat-up until the resistivity increases above a predetermined set point where the band is dry or clean of the fouling material. That temperature is also measured and recorded against a fouling index. The cooling cycle is repeated until minimum resistivity is again measured. The fouling index can be a table of data developed from the particular furnace or a set of furnaces over time. The data correlates ammonia slip concentration to fouling temperature and also correlates fouling temperature to the amount of deposit that is likely occurring on the heat exchanger. The integral of temperature change divided by resistivity determines the severity of fouling and therefore the relative amount of ammonia which must be limited at that spatial area. The user can the adjust the ammonia injectors responsible for the ammonia in the area when the probe was positioned. Resistivity is high until a distinct change occurs when liquid ammonium bisulfate forms on the measurement band. Then the lowering of resistivity may result from characteristics of chloride, water, $SO_3$ and ammonia concentration. Both the temperature of initial resistivity change and the liquid/solid resistivity as the water dew point is reached are characteristics of the fuel sulfur and ammonia concentrations.

The monitor 9 should have a clock and the capability to receive temperature readings from the thermocouple 5. Consequently, a time and temperature profile can be developed and correlated to changes in resistance and electrochemical activity. This information could then be compared to ammonia injection rates as well as to burner operation. If excess ammonia is detected by the probe one or more ammonia injectors could be adjusted. It may also be possible to overcome the problem through a change in burner operation, particularly if a burner had been shut down and the shut down is correlated to the presence of excess ammonia.

Figure 3:
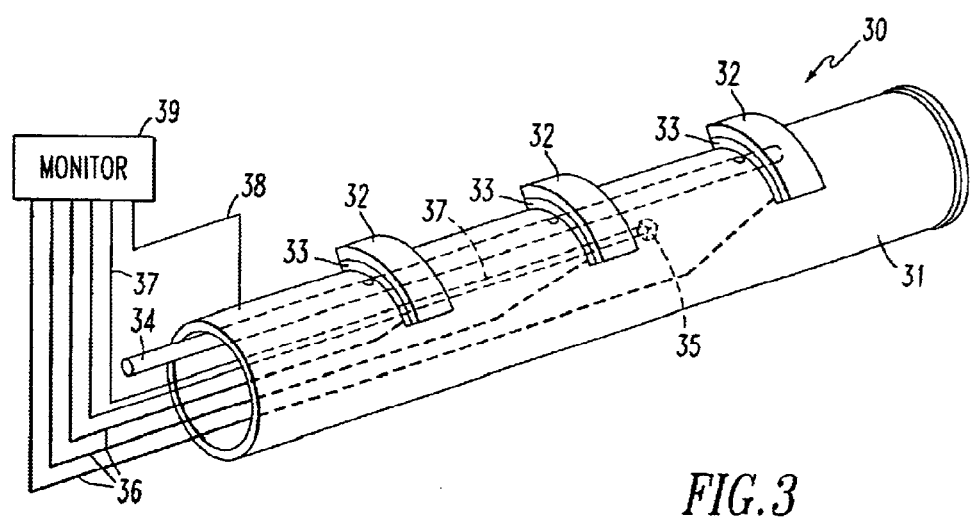
FIG. 3 is a perspective view of a second present preferred embodiment of a probe in accordance with the present invention.

Another embodiment of our invention is shown in FIG. 3. In this embodiment the air-cooled probe 30 consists of multiple insulated patches 32 made of the same material as the tubular probe body 31, but electrically insulated by an adhesive insulating material 33. Spaced apart bands 33 of each patch 32 form the electrodes, which are connected to a corrosion monitor 39. A single air cooling tube 34 or series of tubes (not shown) provides cooling air to the region around each patch. At least one thermocouple 35, monitor wires 36 connected to the bands 23, monitor wire 38 connected to the probe body, and thermocouple wires 37 are provided and function as in the embodiment of FIG. 1.

Although we have shown and described certain present preferred embodiments of our method and apparatus for detecting excess ammonia in flue gas it should be distinctly understood that our invention is not limited thereto but may be variously embodied within the scope of the following claims.

We claim:

1. A method of measuring ammonia concentration in a flue gas stream containing at least a few hundred parts per million of sulfur dioxide and sulfur trioxide and into which flue gas stream ammonia has been injected and reacts to form ammonium sulfates comprising:
   a. placing in the flue gas stream at least one pair of electrodes which are physically close but not touching, thereby forming a gap between the electrodes;
   b. electrically connecting the electrodes to a device to measure resistance in a circuit formed when ammonia sulfates are deposited from the flue gas closing the gap between the electrodes;
   c. measuring the resistance between the electrodes; and
   d. determining an ammonia concentration level in the flue gas from the measured resistance.

2. The method of claim 1 wherein the electrodes are attached to a probe.

3. The method of claim 2 also comprising cooling the probe so that the gap between the electrodes is at a temperature below 914° F. and above 296° F.

4. The method of claim 3 also comprising periodically measuring a temperature within the gap and adjusting the cooling step as dictated by the temperature.

5. The method of claim 4 wherein the cooling is performed in a manner to give a selected time-temperature profile.

6. The method of claim 2 also comprising heating the probe to a temperature above 914° F.

7. The method of claim 1 comprising determining at least one temperature at which the resistance falls very rapidly and selecting that at least one temperature as an indicator of the ammonia concentration.

8. The method of claim 1 wherein the ammonia is injected through various nozzles into the flue gas stream further comprising adjusting a flow of ammonia through at least one nozzle in accordance with the resistance measured across the electrode gap.

9. The method of claim 8 wherein the adjustments are made to maximize total resistance between all of the gaps while maintaining a constant total ammonia flow.

10. The method of claim 1 wherein there are a plurality of pairs of electrodes and each pair of electrodes is attached to a probe.

11. The method of claim 10 also comprising cooling the probes so that the gap between the electrodes is at a temperature below 914° F. and above 296° F.

12. A method of measuring fouling potential of ammonia, sulfur dioxide and sulfur trioxide in flue gas comprising:
   a. placing in the flue gas at least one pair of electrodes which are physically close but not touching, thereby forming a gap between the electrodes;

b. electrically connecting the electrodes to a device to measure resistance in a circuit formed when ammonia sulfates are deposited from the flue gas closing the gap between the electrodes;

c. measuring the resistance between the electrodes; and d. determining a fouling potential from the measured resistance.

13. The method of claim 12 wherein the electrodes are attached to a probe.

14. The method of claim 13 also comprising cooling the probe so that the gap between the electrodes is at a temperature below 914° F. and above 296° F.

15. The method of claim 14 also comprising periodically measuring a temperature within the gap and adjusting the cooling step as dictated by the temperature.

16. The method of claim 15 wherein the cooling is performed in a manner to give a selected time-temperature profile.

17. The method of claim 13 also comprising heating the probe to a temperature above 914° F.

18. The method of claim 12 comprising determining at least one temperature at which the resistance falls very rapidly and selecting that at least one temperature as an indicator of fouling.

19. The method of claim 12 wherein the ammonia is injected through various nozzles into the flue gas further comprising adjusting a flow of ammonia through at least one nozzle in accordance with the resistance measured across the electrode gap.

20. The method of claim 19 wherein the adjustments are made to maximize total resistance between all of the gaps while maintaining a constant total ammonia flow.

21. The method of claim 12 wherein there are a plurality of pairs of electrodes and each pair of electrodes is attached to a probe.

22. The method of claim 21 also comprising cooling the probes so that the gap between the electrodes is at a temperature below 914° F. and above 296° F.

* * * * *